(12) United States Patent
Carlessi et al.

(10) Patent No.: US 8,106,241 B2
(45) Date of Patent: Jan. 31, 2012

(54) ENHANCED PROCESS FOR THE SYNTHESIS OF UREA

(75) Inventors: Lino Carlessi, Dalmine (IT); Alessandro Gianazza, Legnano (IT)

(73) Assignee: Saipem S.p.A., San Donato Milanese (IT)

( * ) Notice: Subject to any disclaimer, the term of this patent is extended or adjusted under 35 U.S.C. 154(b) by 145 days.

(21) Appl. No.: 12/601,103

(22) PCT Filed: May 19, 2008

(86) PCT No.: PCT/EP2008/004119
§ 371 (c)(1),
(2), (4) Date: Mar. 26, 2010

(87) PCT Pub. No.: WO2008/141832
PCT Pub. Date: Nov. 27, 2008

(65) Prior Publication Data
US 2010/0217041 A1    Aug. 26, 2010

(30) Foreign Application Priority Data
May 22, 2007 (IT) .............................. MI2007A1029

(51) Int. Cl.
*C07C 273/04* (2006.01)
(52) U.S. Cl. ............................... 564/70; 564/71; 564/72

(58) Field of Classification Search .................... 564/70, 564/71, 72
See application file for complete search history.

(56) References Cited

U.S. PATENT DOCUMENTS

| 3,137,724 A | 6/1964 | Guyer et al. |
| 4,801,745 A | 1/1989 | Meessen et al. |

FOREIGN PATENT DOCUMENTS

| EP | 0 212 744 | 3/1987 |
| GB | 1 341 497 | 12/1973 |

*Primary Examiner* — Peter O Sullivan
(74) *Attorney, Agent, or Firm* — Oblon, Spivak, McClelland, Maier & Neustadt, L.L.P.

(57) ABSTRACT

An enhanced process is described for the synthesis of urea from ammonia and carbon dioxide, at a high pressure and temperature, with the formation of ammonium carbamate as intermediate, which includes a high pressure synthesis section, comprising at least one separation step by decomposition-stripping with ammonia of the non-converted ammonium carbamate, carried out in a vertical apparatus, commonly called stripper, characterized in that said step also comprises a feeding, in the lower part of said stripper, of a stream of $CO_2$, heated to a temperature ranging from 130 to 230° C., in a quantity of 1 to 15% by weight with respect to the total weight of the fresh $CO_2$ fed to the process, containing a passivating agent in such a quantity that its equivalent content of $O_2$ in moles varies from 0.05% to 0.80% with respect to the moles of $CO_2$ of said stream.

22 Claims, 2 Drawing Sheets

ENHANCED PROCESS FOR THE SYNTHESIS OF UREA

Figure 1:
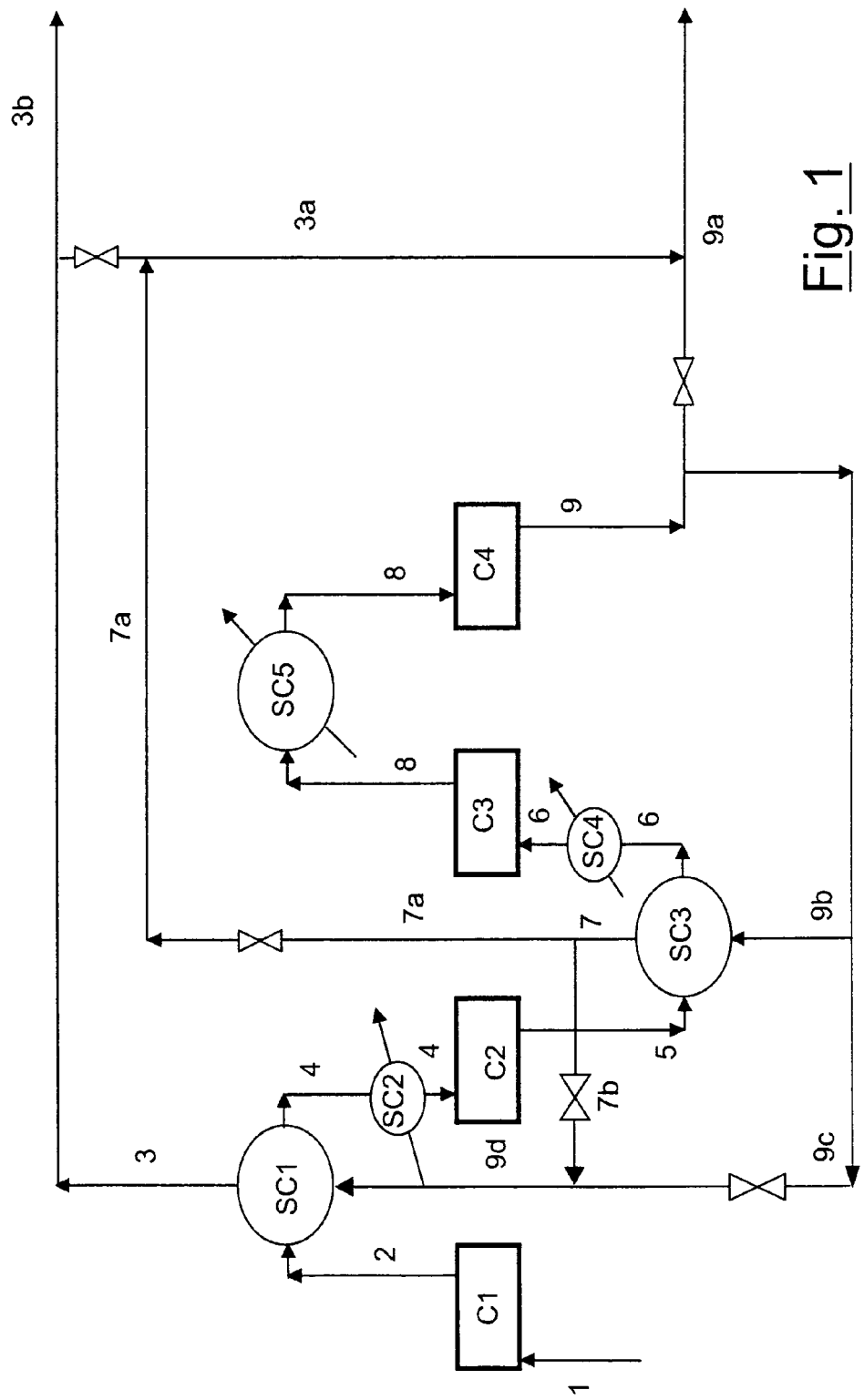

The present invention relates to an enhanced process for the synthesis of urea.

In particular, several processes for the production of urea are known in the state of the art.

The synthesis of urea is effected by the reaction of ammonia and carbon dioxide at a high pressure and temperature, the subsequent separation of urea from the mixture containing the non-reacted products and recycling of the same to the reactor.

All industrial processes for the preparation of urea, are therefore based on direct synthesis according to the following reaction:

$$2NH_3 + CO_2 \leftrightarrow CO(NH_2)_2 + H_2O \qquad (1)$$

This synthesis takes place in two different reaction steps:

$$NH_3 + CO_2 \leftrightarrow (NH_2)COONH_4 \qquad (1a)$$

$$(NH_2)COONH_4 \leftrightarrow CO(NH_2)_2 + H_2O \qquad (1b)$$

In the first step (1a) an exothermic equilibrium reaction takes place having a high reaction rate at room temperature, which, however, needs high pressures to reach a favourable equilibrium at the high temperature required by step (1b).

In the second step (1b), an endothermic reaction occurs, which reaches a considerable rate only at high temperatures (>150° C.), with an equilibrium state which, at 185° C., starting from a mixture of reagents in a stoichiometric ratio, leads to a $CO_2$ conversion slightly higher than 50%. This unsatisfactory conversion can be suitably enhanced by increasing the $NH_3/CO_2$ ratio.

The above two steps do not normally take place in separate areas of the reactor, but contemporaneously in the reaction mixture, which therefore includes, urea, water, ammonia, carbon dioxide and ammonium carbamate, with a relative concentration, in the different points of the reactor, depending on the different thermodynamic and kinetic factors which contribute to the process.

Processes for the production of urea by direct synthesis starting from ammonia and carbon dioxide are widely described in specific literature relating to the field. A large survey of the most common processes for the production of urea can be found, for example, in the publication "Encyclopedia of Chemical Technology" Ed. Kirk-Othmer, Wiley Interscience, third Ed. (1983), vol. 23, pages 548-575.

Industrial processes for the production of urea normally carry out the synthesis in a reactor fed with $NH_3$, $CO_2$ and with aqueous solutions of ammonium carbamate and/or carbamates coming from the recycled streams of the unconverted reagents, at temperatures ranging from 150 to 215° C., at pressures of at least 13.2 MPa (130 atm), with a $NH_3/CO_2$ molar ratio ranging from 2.5 to 5, calculated with respect to the sum of the feeding streams, including ammonia and $CO_2$, in the form of ammonium carbamate/carbonate. In addition to the water formed and excess of $NH_3$ fed, the effluent from the reactor still has considerable amounts of $CO_2$, mainly in the form of unconverted ammonium carbamate.

The control of the thermal level in the reactor is also an essential aspect for obtaining an optimal conversion, as temperatures which are either too low or too high lead to a reduction in the conversion due to the concurrence of various chemical and thermodynamic factors.

The separation of urea from the water and unconverted reagents is carried out in several sections operating at decreasing temperatures and pressures, in which the decomposition is effected of ammonium carbamate to $NH_3$ and $CO_2$, which are then made available for recycling to the reactor. The carbamate separation and recycling section has investment costs which heavily influence the cost of the final product.

Known processes which operate according to the above general scheme are described, for example, in U.S. Pat. No. 4,092,358, U.S. Pat. No. 4,208,347, U.S. Pat. No. 4,801,745 and U.S. Pat. No. 4,354,040.

In particular, the urea contained in the aqueous solution leaving the reactor is separated from most of the non-transformed ammonium carbamate and from the excess ammonia used in the synthesis in suitable decomposers or strippers which operate at pressures substantially equal to or slightly lower than the synthesis pressure.

The decomposition of ammonium carbamate is effected in the decomposers by supplying heat from the outside by means of indirect thermal exchange with a warmer fluid, normally vapour at 1.8-3.0 MPa, possibly stripping the decomposition products with inert gasses or ammonia or carbon dioxide or blends of inert gases with ammonia and/or carbon dioxide, the stripping possibly being effected using the excess ammonia, dissolved in the urea solution (self-stripping) consequently without separately feeding the stripping agent.

The carbamate decomposition products, together with the possible stripping agents, with the exception of inert products, are normally condensed in condensers, obtaining a liquid which is recycled to the synthesis reactors.

Further documents which can be mentioned for reference purposes, are U.S. Pat. No. 4,314,077, GB 1,184,004, GB 1,292,515, U.S. Pat. No. 3,984,469, U.S. Pat. No. 4,137,262, DE 2,116,267, FR 2,489,323, which describe processes for the production of urea having the above-mentioned characteristics.

Particularly delicate steps in the urea synthesis process are those in which the ammonium carbamate is present at the highest temperature and concentration and consequently in the processes mentioned above these steps coincide with the decomposition-stripping steps and condensation of ammonium carbamate.

One of the problems to be solved in these steps relates to the corrosion of the equipment involved due to the extremely aggressive characteristics which are created in their interior, both for the presence of saline solutions at a high concentration and phenomena due to mechanical stress of the surfaces in the decomposition areas and release of the gaseous phase.

To overcome these drawbacks, the known art suggests, for example, the use of special materials in the production of the stripper, particularly Ti, Zr, special stainless steels, urea grade, or a combination of the same. Still according to the state of the art, it is advantageous to feed a certain amount of air or other passivation agent, to prolong the resistance to corrosion of the materials, especially stainless steels, favouring the formation of a stable layer of oxide on the surfaces exposed to contact with the process fluids.

In particular, the present invention can be inserted within the specific field of plants for the synthesis of urea with ammonia stripping, i.e. in plants in which the stripping action is facilitated in the stripper, in which the decomposition of carbamate takes place, by the ammonia present in the synthesis solution and/or by the ammonia fed for the purpose.

At present, in this type of plant, a certain quantity of air is added to the bottom of the stripper, in order to obtain the passivation of the stainless steel stripper. This addition is effected by means of a suitable injection of air by means of compressors prepared exclusively for this purpose. In the other parts of the high pressure urea synthesis loop which requires passivation, this passivation is still obtained with air which is mixed at the inlet of the $CO_2$ compressor and is sent to the urea reactor by means of the compressor itself. The air which has not participated in the passivation reaction of the reactor, flows out of the reactor together with the reaction mixture and is sent to the upper part of the stripper, from which it passes to the carbamate condenser and from there to the carbamate separator, consequently leaving the synthesis loop by means of the valve destined for the control of the pressure of the loop itself.

During this passage, the air effects the passivation of the surfaces of the equipment it encounters which would otherwise be exposed to corrosion processes.

In consideration of what mentioned above, i.e. the fact that the passivation air is sent from the reactor to the upper part of the stripper, the bottom of the stripper is excluded from the passivation action exerted by said air which is mixed at the inlet of the $CO_2$ compressor and sent to the reactor by means of the compressor itself.

For this reason, the known art describes the necessity of effecting a suitable injection of air by means of compressors destined for this purpose only.

This solution however necessitates further specific devices, i.e. said compressors, which, in addition to the cost, also require periodical maintenance interventions.

As previously mentioned, a further aspect to be considered in these plants is linked to the fact that the heat developed, and, more generally, the thermal level of the reactor in the feeding and reaction step of ammonia and carbon dioxide, with the formation of a liquid mixture containing ammonium carbamate, water, ammonia and urea, is controlled by operating on the thermal level of the $CO_2$ and/or ammonia streams, fed to the reactor and/or on the basis of the distribution of the same feeding streams between stripper, condenser and reactor and/or on the amount of heat removed in the condenser. This control of the thermal level is a further essential aspect for obtaining an optimal conversion in the reactor, as temperatures which are both too low and too high lead to a reduction in the conversion due to the concurrence of various chemical and thermodynamic factors.

A process has now been found by the applicant, which overcomes the drawbacks pertaining to the state of the art, described above, and further optimizes the synthesis process of urea.

An object of the present invention therefore relates to an enhanced process for the synthesis of urea from ammonia and carbon dioxide, at a high pressure and temperature, with the formation of ammonium carbamate as intermediate product, which includes a high pressure synthesis section, comprising at least one separation step by decomposition-stripping with ammonia of the unconverted ammonium carbamate, carried out in a vertical apparatus, commonly called stripper, characterized in that said step also includes a feeding of a $CO_2$ stream, in the lower part of said stripper, heated to a temperature ranging from 130 to 230° C., preferably from 150 to 210° C., in a quantity ranging from 1 to 15%, preferably from 3 to 12% by weight, with respect to the total weight of the fresh $CO_2$ fed to the process, containing a passivating agent in such an amount that its equivalent content of $O_2$ in moles ranges from 0.05% to 0.80%, preferably from 0.10 to 0.40%, with respect to the moles of $CO_2$ of said stream.

In the present description, the term "heating, heated" referring to a stream of $CO_2$ means that said stream was subjected to an increase in temperature and has a temperature higher than the temperature of the $CO_2$ stream at the outlet of the final delivery of the compressor.

More preferably, the heated $CO_2$ stream fed to the stripper envisages a temperature ranging from 160 to 200° C.

According to the present invention, the fresh $CO_2$ not fed to the stripper, is preferably sent to the reactor, but can also be partialized between the reactor and other steps of the process, such as the condenser and one or more separation steps at medium and low pressure.

Preferably, said heated $CO_2$ stream fed to the stripper is in a quantity ranging from 4 to 15%, more preferably from 4 to 12% by weight with respect to the total weight of the fresh $CO_2$ fed to the reactor.

The compressed $CO_2$ stream fed to the reactor has a temperature ranging from 100 to 200° C., preferably from 130 to 185° C.

The total compressed $CO_2$ can be subjected to heating, or the $CO_2$ stream alone to be fed to the stripper can be subjected to heating.

Preferably, the $CO_2$ stream fed to the stripper is heated in one or more of the intersteps of the $CO_2$ compressor.

The compressed $CO_2$ stream fed to the reactor can also consist of a mixture in suitable percentages of a stream of compressed $CO_2$ and of one or more heated streams of $CO_2$ respectively, in one or more of the intersteps of the $CO_2$ compressor in delivery to the reactor, even more preferably, of a blend, in suitable percentages, of a compressed $CO_2$ stream and a heated $CO_2$ stream, at least in the interstep of the compressor which has the highest thermal level.

According to a particular embodiment of the present invention, the $CO_2$ stream sent to the reactor, having a temperature ranging from 130 to 185° C., consists, for a quantity ranging from 0 to 40% by weight with respect to the total weight of said stream, of compressed $CO_2$ leaving the reactor at a temperature ranging from 100 to 120° C. and for a quantity ranging from 60 to 100% by weight with respect to the total weight of said stream, of a stream of heated $CO_2$ in one or more of the heat exchange inter-steps of the compressor up to a temperature ranging from 140 to 200° C.

According to another preferred embodiment of the present invention, the fresh $CO_2$ stream fed to the stripper, which represents from 4 to 12% by weight of the $CO_2$ sent to the reactor, is heated to a temperature ranging from 160 to 200° C., in one or more of the heat exchange inter-steps of the $CO_2$ compressor.

The $CO_2$ stream subjected to heating, is heated in one or more of the intersteps of the $CO_2$ compressor, in delivery to the reactor, at the external side or tube side.

The decomposition-stripping step of ammonium carbamate with ammonia is preferably a self-stripping step.

The passivating agent is generally an oxidant which is preferably selected from air, oxygen, enriched air, hydrogen peroxide or mixtures thereof, preferably air.

The term "equivalent content of $O_2$" as used herein with reference to the passivating agent, identifies the $O_2$ moles which it would be necessary to use instead of the passivating agent for obtaining the same conversion in a redox reaction. It corresponds to the $O_2$ moles, in the case of air or oxygen, to half of the $H_2O_2$ moles and 3/2 of the ozone moles.

The process according to the present invention preferably comprises a synthesis phase of urea, wherein the ammonia/carbon dioxide molar ratio ranges from 2.7 to 5.0, more preferably from 3.0 to 4.0.

A fundamental advantage of the enhanced process according to the present invention is that it allows a contemporaneous optimization of the processability of the reactor and stripper.

Bearing in mind that the regulation of the reactor temperature is fundamental for the optimization of the conversion and that the $CO_2$ stream is specifically heated to have an optimal conversion in the reactor, it should in fact also be remembered that excess heating leads to a reduction in the conversion. This control of the thermal level is therefore also advantageously obtained by sending an aliquot of the heated $CO_2$ stream to the stripper and, consequently at the same time, the processability of both the reactor and the stripper is optimized.

By sending an aliquot of the heated $CO_2$ stream to the stripper and, at the same time, increasing the temperature of the compressed $CO_2$ stream fed to the reactor to counterbalance the decrease in quantity, extremely advantageous effects are obtained contemporaneously: the reactor operates at the optimal temperature to maximize the conversion, whereas, by passivation on the part of the passivating agent, in particular air, present in the heated $CO_2$ stream, the corrosion of the bottom of the stripper is prevented. This solution also leads to a recovery of heat, thus allowing a further enthalpic increase which gives an added value to the process according to the invention. In addition, the reactor can operate at the optimal temperature also heating the ammonia stream being fed to the same.

A further advantage of the process according to the present invention consists of the elimination of compressors destined for sending passivation air to the bottom of the stripper, which represent a cost and require periodical maintenance.

The present process also has the advantage of being easily and surprisingly effected by making a few, simple modifications in an already existing traditional plant, provided it has a high-pressure stripping section. In particular, it is sufficient to modify the plant so as to send to said stripping section a heated $CO_2$ stream in delivery of the $CO_2$ compressor to the reactor.

Figure 2:
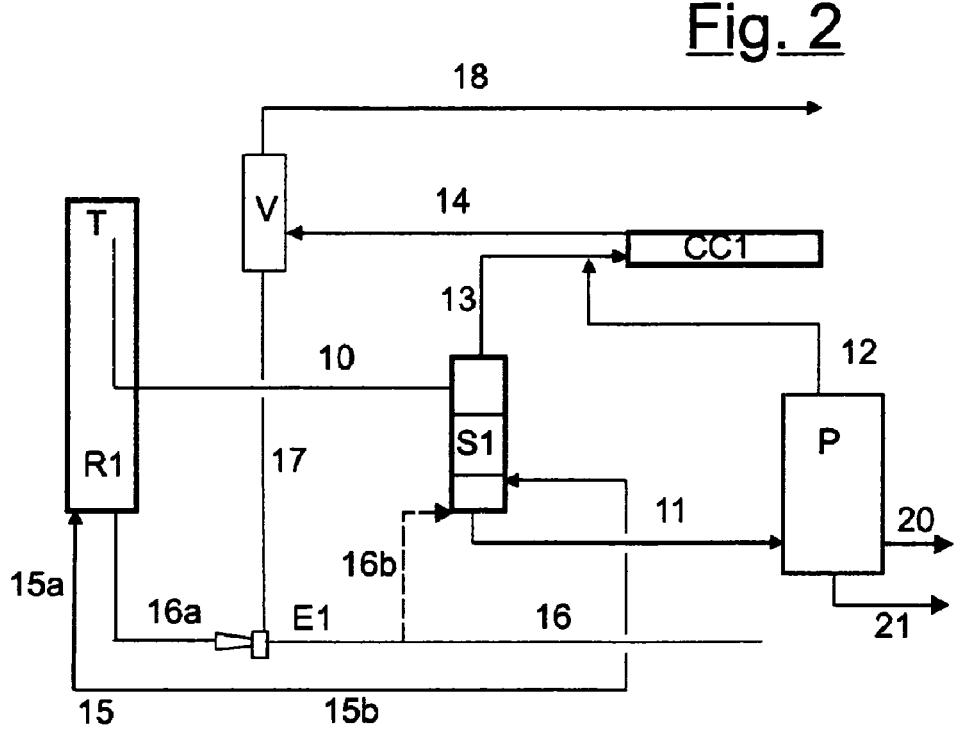

A further advantage is the possibility of using the stripper in any urea-resistant steel material. The process according to the present invention is further illustrated by means of the enclosed figures, in which:

FIG. 1 schematically represents an embodiment of the compression and pre-heating steps of the $CO_2$ stream;

FIG. 2 schematically represents the embodiment of the reaction steps and decomposition-stripping (synthesis loop) of a process for the synthesis of urea, which represents a preferred embodiment of the present invention.

Figure 3:
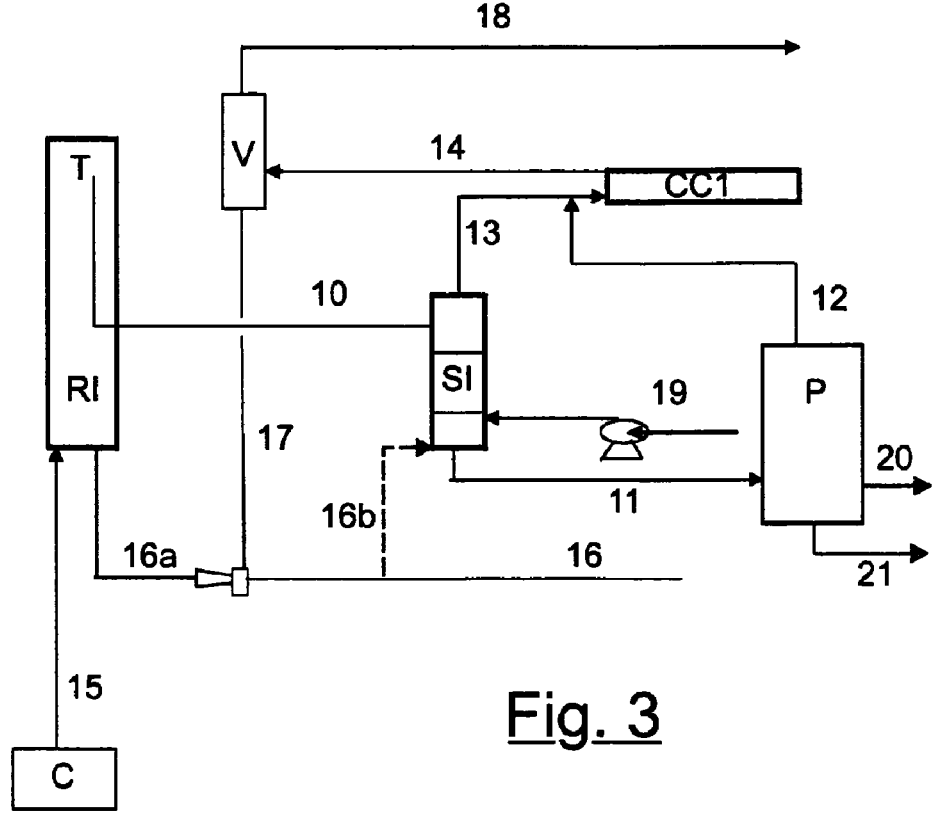

FIG. 3 schematically represents the embodiment of the reaction steps and decomposition-stripping (synthesis loop) of a process for the synthesis of urea, according to an embodiment of the state of the art.

The functional details, such as pumps, valves and other equipment not necessary for the full understanding of the processes schematized are not shown in the above-mentioned figures. In no case should the process according to the present invention be considered as being limited to what is shown and described in the enclosed figures, which are provided for illustrative purposes only.

In the process according to the present invention, in which the reactor operates with an excess of ammonia with respect to the stoichiometric ratio with carbon dioxide necessary for producing ammonium carbamate and subsequently urea, the stream leaving the reactor and, in general, most of the liquid streams formed in the process, normally contain ammonia in excess. During the present description, reference is made to the composition of these liquid streams and mixtures (also biphasic), conventionally considering that all of the carbon dioxide is present in the form of ammonium carbamate, and the remaining excess of ammonia is present as free ammonia, or, more simply, ammonia.

Furthermore, in order to simplify the present description, the term "liquid" is used with reference to streams of mixtures consisting of a single liquid phase or a mixed liquid-vapour phase. The term "gaseous" is used, on the contrary, for streams or mixtures in which the liquid phase is substantially absent.

In the scheme of FIG. 1, the successive compression steps can be distinguished, C1, C2, C3 and C4 and the exchangers SC1, SC2, SC3, SC4 and SC5. The compression step C1, fed by line 1, is connected, through line 2, to a first exchanger SC1, having the highest thermal level, wherein the compressed $CO_2$ of the line 9d is heated and sent to the exit line 3 which is directly connected to the stripper S1 through the line 3b (15b in FIG. 2). The $CO_2$ coming from line 2 is cooled and leaves SC1 through line 4 which is connected to the second compression step C2, after passing through the exchanger SC2 (equipped with cooling water). The $CO_2$ leaving the compression step C2 is fed through line 5 to the exchanger SC3 from which it exits through line 6 to be connected with the compression step C3, after passing through the exchanger SC4 (equipped with cooling water). Cooling $CO_2$ is fed to the other side of the exchanger SC3, through the line 9b, which exits through line 7 and can be sent to the exchanger SC1 by means of lines 7b and 9d, and to the reactor, through line 7a, which is connected to line 3a and, subsequently, to line 9a (corresponding to 15a in FIG. 2). Line 3 is also connected to line 3a, which comes from the exchanger SC1 for a possible partialization between the reactor and the $CO_2$ stripper with the highest thermal level.

The compression step C3 is then connected, by means of line 8 and after passing through the exchanger SC5 (equipped with cooling water), to the compression step C4, which, in turn, includes an exit line 9 which connects it directly to the exchanger SC3 by means of line 9b and to the reactor R1, through line 9a (15a in FIG. 2). Step C4 can also be directly connected to the exchanger SC1 through lines 9, 9c and 9d in succession.

The connection lines schematized in FIG. 1 allow, through the regulation of the valves indicated by means of the butterfly symbol, various flow compositions to be produced in order to obtain, for the $CO_2$ being fed to the reactor and stripper, the thermal levels and flow-rates selected in accordance with the present invention. In the embodiment of the present invention, some of the lines shown in FIG. 1 can, when necessary, be unused.

The scheme of FIG. 2 shows the reactor R1, which is connected, through the overflow T and line 10, with the stripper S1. The latter is connected, through line 11, with the urea separation and purification section P, from which, through line 12, carbamate is recycled to the condenser CC1 and urea is obtained, pure, solid or in aqueous solution, through line 20. The outlet of the gases from the stripper S1 is connected to the condenser CC1 through line 13. The outlet of the condenser CC1 is represented by line 14, which is then connected to the separator.

The compression and heating unit of the carbon dioxide C is connected to the reactor (line 15a) and to the bottom of the stripper (line 15b). Line 16a is the feeding line of ammonia to the reactor, consisting of the feeding line of fresh and recovered ammonia 16, and the recycling line of the carbamate 17, at the outlet of the separator V. At the head of the separator V an outlet line 18 is envisaged for the discharge of inert products and for pressure control.

The scheme shown in FIG. 3 substantially reproduces the same elements, with the same meaning, of the scheme of FIG. 2. This refers however to a traditional process for the synthesis of urea. The significant difference with respect to FIG. 2 consists in the absence of line 15b with the total feeding of fresh $CO_2$ to the reactor, through line 15 coming from the compression unit C, and in the presence of a compressor 19 destined for feeding passivation air to the bottom of the stripper S1.

The process according to the present invention can be effected in a plant having the above-mentioned characteristics, equipped with a synthesis section comprising the equipment and connections previously mentioned with reference to the scheme of FIG. 2. This plant can be obtained as such starting from a new construction, or it can be simply and conveniently obtained by modifying a pre-existing plant for the synthesis of urea, equipped with a stripper suitable for operating under self-stripping conditions, by means of a connecting line between the $CO_2$ compressor and the lower section of said stripper, suitable for feeding a $CO_2$ stream to the stripper, in a quantity ranging from 1 to 150, preferably from 4 to 12% by weight, with respect to the total weight of the fresh $CO_2$ fed to the plant.

With reference to FIGS. 1 and 2, various possible embodiments of the process of the present invention are now described, said description however being non-limiting of the overall scope of the invention itself.

The fresh $CO_2$ stream is fed to the compression and heating unit C represented in detail in FIG. 1.

This unit, which represents the delivery compressor of the reactor, consists of a series of compression steps (normally four), at progressively higher pressures, intervalled by the same number of thermal exchange steps for the regulation of the temperature of the $CO_2$. The pressures reached in the different compression steps depend on the construction and operative characteristics of the compressors and are normally known to technical experts in the art. The methods for the embodiment of the thermal exchange intersteps coupled with the compression steps, are also known.

According to a particular embodiment, all the compressed $CO_2$ stream, through the four compression steps C1, C2, C3 and C4, by means of lines 2, 4, 5, 6 and 8, is sent, through lines 9 and 9b, to the exchanger SC3. The exchanger SC3 envisages that the $CO_2$ stream at the outlet through line 7, which is further heated, be partially sent, by means of lines 7b, to line 9d which feeds the exchanger SC1, and subsequently to the stripper S1 by means of lines 3 and 3b, and for the most part, through line 7a, it is conveyed to line 3a and from there sent directly to the reactor R1, by means of line 9a.

Alternatively, it is also possible to send all the compressed $CO_2$ stream coming from the exchanger SC3 to the exchanger SC1, through lines 7, 7b and 9d, and from there, after further heating, it is partially sent, through line 3, to the stripper S1, and, for the most part, to the reactor R1 by means of lines 3a and 9a.

According to another alternative, the compressed $CO_2$ stream, through passage in the four compression steps C1, C2, C3 and C4, by means of lines 2, 4, 5, 6 and 8, is partially sent, by means of lines 9 and 9a, directly to the reactor R1, and partially, by means of line 9b to the exchanger SC3. At the outflow of the exchanger SC3, the $CO_2$ stream, further heated, can follow one of the routes described in the previous paragraphs.

According to another alternative, the compressed $CO_2$ stream at the outlet of step C4 by means of line 9, is partially sent directly to the exchanger SC3 through lines 9c and 9d, and from this point to the stripper, through lines 3 and 3b, and for the most part to the exchanger SC3 and from there to the reactor R1, through lines 7, 7a, 3a and 9a.

According to the scheme of FIG. 2, the fresh and recovered ammonia, compressed and fed through line 16, are sent as force fluids to the ejector E1, and are mixed here with the recovery and recycled stream (line 17), containing ammonia, carbamate and water, coming from the separator V and comprising the condensate produced in CC1 and the recovered product coming from section P. The resulting stream is sent to the reactor R1 through line 16a.

Alternatively, according to requirements, a part of the ammonia can be fed to the stripper S1 (through line 16b).

Under the normal operative process conditions according to the present invention, the above-mentioned streams mainly contain ammonia in the liquid state.

The fresh $CO_2$ containing the passivating agent which can be air, for example, is sent, through lines 15a and 15b, to the reactor R1 and to the stripper S1 respectively.

Most of the fresh carbon dioxide, after compression, is sent directly to the reactor (over 85%) and is partially fed to the stripper S1, as previously explained in detail with reference to FIG. 1.

The overall feeding of the reactor consists of streams 15a and 16a, in turn fed by the recycled line 17.

The liquid stream discharged from the reactor R1 by means of the overflow T and line 10, containing urea, water, ammonia, ammonia carbamate and air, is fed to the stripper S1.

The recovered stream coming from unit P and containing water, ammonia and ammonium carbamate is sent to the condenser CC1, through line 12.

The gaseous stream 13 discharged from the head of the stripper S1, containing $NH_3$, $CO_2$ and water, is recycled to the condenser CC1. It is condensed therein, at a pressure similar to or slightly lower than that of the reactor and at the highest possible temperature, preferably higher than 140° C., and more preferably from 150 to 180° C., to obtain a liquid stream mainly containing ammonium carbamate and ammonia, and smaller amounts of water and, possibly, urea. The latter is formed during the condensation step, the operative conditions already being favourable for partially shifting the chemical equilibrium (1b) previously mentioned, to the right. The liquid stream thus obtained is fed to the separator V through line 14. A gaseous stream comprising inert gases and possibly residual oxygen in addition to small amounts of ammonia, $CO_2$ and $H_2O$ is flushed from the head of the separator V, through line 18.

The stream 11, discharged from the bottom of the stripper S1, containing all the urea produced, is sent (line 11) to the subsequent purification and concentration steps, which are schematically combined in section P of FIG. 2. The stream of $NH_3$, carbamate and recovered water (stream 12) already mentioned above, comes from this point, and pure urea and water are recovered, through lines 20 and 21, respectively.

The enhanced process for the synthesis of urea from ammonia and carbon dioxide according to the present invention, is used, for example, in a synthesis process comprising the following phases:

(a) feeding and reacting ammonia and carbon dioxide in at least one reactor, with a $NH_3/CO_2$ molar ratio, as such or as ammonium carbamate, ranging from 2.7 to 5, preferably from 3.0 to 4.0, with the formation of a first liquid mixture containing ammonium carbamate, water, ammonia and urea;

(b) transferring said first liquid mixture to a decomposition-stripping step;

(c) heating this first liquid mixture in said decomposition-stripping step, by substantially operating at the same pressure as said reactor, to obtain the decomposition of part of the ammonium carbamate into ammonia and carbon dioxide, simultaneously subjecting said liquid mixture to stripping with ammonia, with the formation of a first gaseous mixture containing ammonia, carbon dioxide and water, and a second liquid mixture containing urea, water, ammonia and the non-decomposed part of ammonium carbamate; a heated $CO_2$ stream containing a passivating agent also being fed to the bottom of the stripper, (d) transferring, possibly through an ejector, said first gaseous mixture to a condensation step substantially operating at the same pressure as the reactor, and condensing the same mixture with the formation of a third liquid mixture containing ammonium carbamate and ammonia, which is sent to a separator;

(e) recovering the urea contained in said second liquid mixture, in one or more subsequent decomposition and separation steps with the formation of substantially pure urea, a fourth liquid mixture containing water, ammonia and ammonium carbamate and, possibly, a fifth stream substantially containing ammonia, said fourth liquid mixture formed in step (e) being sent to said condensation step.

This synthesis process is normally carried out in continuous in a suitable plant, fresh ammonia and carbon dioxide are continuously fed to the plant to balance the corresponding amount of reagents transformed into urea and removed at the outflow of the final separation and "prilling" section.

The fresh ammonia can be fed directly to the reactor, or it can be sent, partially or totally, as stripping fluid into the stripper and/or sent directly to the condenser.

The ammonia compressed and fed to the reactor has a temperature generally ranging from 0 to 130° C., preferably from 30 to 100° C. A greater thermal content of the ammonia stream can be preferred if a quantity of fresh $CO_2$ ranging from 8 to 15% of the total is fed to the stripper, in order to maintain a satisfactory thermal level in the reactor.

The synthesis reactor normally operates at temperatures ranging from 150 to 215° C., preferably from 160 to 195° C., and at pressures ranging from 8.9 MPa to 20 MPa, preferably from 11 MPa to 18 MPa, with ammonia/carbon dioxide molar ratios preferably ranging from 2.7 to 5.0, more preferably between 3.0 and 4.0.

The regulation of the temperature of the reactor to the desired level can be effected according to any of the methods known in the art, for example, in addition to the above-mentioned heating of the ammonia stream in the feeding, by providing the reactor with a heating resistance, or by sending part of the gases coming out the stripper, directly to the reactor.

The reactor is normally equipped with several plates, of a typology selected from those known in the art, in order to provide the optimal plug flow conditions, possibly also in the presence of biphasic systems.

The reactor can also include various reaction zones, suitably interconnected with each other, possibly having different feeding streams.

The reactor must have a liquid hold-up which is such as to allow a residence time of the same ranging from a few minutes to several tens of minutes, to allow the ammonium carbamate formed by the reaction of ammonia with carbon dioxide in the condensation step and/or in the reactor itself, to dehydrate to urea.

The decomposition-stripping step is normally effected in a heated stripper, usually by means of indirect vapour at high pressure. The temperature of the stripper normally ranges from 160 to 220° C., preferably from 190 to 210° C., whereas the pressure is the same or slightly lower than that of the reactor.

Under the above conditions, the ammonium carbamate tends to rapidly decompose, forming ammonia and carbon dioxide, whereas the urea already formed in the reactor remains substantially unaltered. Stripping is carried out using ammonia as carrier gas. In a preferred embodiment of the present invention, the decomposition-stripping step is effected using, as carrier gas, the same ammonia which is in excess in the stream leaving the reactor. Further details on this preferred technology can be found, for example, in U.S. Pat. No. 3,876,696 of SNAMPROGETTI, whose contents are enclosed herewith as reference. This latter technology is called "self-stripping".

The decomposition step is generally effected in tube-bundle equipment, vertically oriented, with a liquid film drop. The mixture leaving the reactor is preferably fed to the head of the equipment and forms a film falling along the walls of the tube bundle. Other known equipment suitable for the purpose can also be used in the process of the present invention.

The condensation step is normally effected in suitable condensers, for example tube-bundle condensers or surface condensers, in which the condensation heat is used for the heating of other fluids. The condensation heat is preferably used for producing vapour, but it can also be used for providing heat to one of the subsequent decomposition steps of the medium- or low-pressure ammonium carbamate.

The condensation step can be carried out under normal conditions (temperature, pressure and composition) used in the known processes, provided the latter are such as to prevent the formation of solid ammonium carbamate in the condenser and/or in the lines leaving the same.

The separation of urea from the ammonia and ammonium carbamate still present in the liquid stream leaving the decomposition-stripping step, is effected in subsequent decomposition and separation sections, operating at medium (from 1.1 MPa to 2.5 MPa) and/or low pressure (from 0.2 to 0.8 MPa). This separation step can be effected by means of any of the methods described in specific literature of the field, which allow a recycled liquid stream containing an aqueous solution of ammonium carbamate and ammonia to be obtained, and possibly also a stream essentially consisting of ammonia. Suitable separation and purification sections are, for example, those schematized in FIGS. 1 to 5 of the publication "Encyclopaedia of Chemical Technology" previously mentioned.

The urea thus separated from the ammonium carbamate and ammonia is generally obtained as an aqueous solution which is subjected to a final vacuum dehydration step (down to 0.001 MPa), obtaining, on the one hand, water and, on the other, substantially pure urea sent to the normal "prilling" processes, etc.

In the separation and purification step of urea, the final dehydration step and purification section of the wastewater leaving the synthesis plant, are also included.

The different liquid or biphasic streams containing ammonium carbamate, coming from the different subsections of the separation and purification step (decomposition of carbamate at medium and low pressure, recondensation of carbamate, dehydration of urea, purification of the wastewater), are collected in a single recycled stream and sent to said condensation step.

According to certain embodiments of the separation and purification of urea, in any case included in the scope of the present invention, the recycled ammonia and carbon dioxide can be present as carbonate, bicarbonate or ammonium carbamate, or a blend thereof, according to the temperature and pressure of the blend.

Some practical examples are provided hereunder for better illustrating the objective and advantages of the present invention, which, however, in no way limit the scope of the claims.

In the following examples, the compositions of the different streams are provided with reference to the base components, urea, ammonia, carbon dioxide and water, regardless of the fact that the carbon dioxide, in the liquid streams containing ammonia, is substantially in the form of ammonium carbamate. Air and inert products are indifferently indicated as "air", as the oxygen consumption under regime conditions in the synthesis cycle is almost negligible.

EXAMPLE 1

A process was carried out for the synthesis of urea, operating according to the present invention, wherein a stream of $CO_2$, containing a suitable amount of air, coming from the compression and heating unit C, was fed to the bottom of the stripper S1. No further quantity of air or other passivating agent was introduced separately at the bottom of the stripper. Reference is made to the schemes shown in FIGS. 1 and 2.

The following components were fed to the reactor R1:
663 kg/hr of $CO_2$ and 5 kg/hr of air from line 15a;
470 kg/hr of $CO_2$, 650 kg/hr of $NH_3$ and 300 kg/hr of water, as ammonium carbamate solution, from line 17;
717 kg/h of pure $NH_3$ from line 16.

The reactor is run at 15.9 MPa and 188° C., the condenser CC1 at 15.4 MPa and about 155° C.

An aqueous stream 12, rich in carbamate, consisting in particular of:
$H_2O$=202 kg/hr
$CO_2$=172 kg/hr
$NH_3$=380 kg/hr
was recovered from the purification and concentration section P, downstream of the stripper S1, which was sent to the condenser CC1 through line 12, after joining the stream 13 coming from the stripper S1.

A gaseous stream 18, consisting of: $H_2O$=2 kg/hr, $CO_2$=2 kg/hr, $Nh_3$=50 kg/hr, air=5.5 kg/hr, was separated in the separator V, from the stream 14, leaving the condenser CC1, the remaining stream 17 being recycled to the reactor R1.

On the whole, the following components were sent to the reactor R1, through line 16a, the formation of urea in the condenser CC1 being formally assumed as null:
$H_2O$=300 kg/hr
$CO_2$=470 kg/hr
$NH_3$=1367 kg/hr The liquid stream 10, discharged from the overflow T of the reactor, containing all the urea produced, was sent to the stripper S1. In particular, it is characterized by the following composition:
Urea=1,000 kg/hr
$H_2O$=600 kg/hr
$CO_2$=400 kg/hr
$NH_3$=800 kg/hr
Air=5 kg/hr.

The stripper runs at 15.2 MPa, at a bottom temperature of 205° C. under self-stripping conditions.

A gaseous stream 13, characterized by the following composition, was discharged from the head of the stripper S1:
$CO_2$=300 kg/hr
$NH_3$=320 kg/hr
$H_2O$=100 kg/hr
Air=5.5 kg/hr.

A stream of $CO_2$, containing air as passivating agent, characterized by the following composition, was fed to the bottom of the stripper, by means of line 15b:
$CO_2$=70 kg/hr
Air=0.5 kg/hr Said $CO_2$ stream was heated in the unit C to a temperature of 197° C. by re-sending an aliquot of the $CO_2$ stream leaving the last compression step to the thermal exchange inter-steps of the same compressor, according to the following scheme, referring to FIG. 1. 733 kg/hr of fresh $CO_2$ in a mixture with 5.5 kg/hr of air were compressed at 16.2 MPa and heated to 110° C. through passage between the four compression steps C1, C2, C3 and C4. 668 kg/hr of this mixture were sent from line 9, by means of line 9b, to the exchanger CS3, which they leave by means of line 7, at a temperature of 165° C. due to the heat exchange with the $CO_2$ stream coming from line 5 at 190° C., which exits at 115° C. by means of line 6. The whole of the $CO_2$ stream of line 7 was fed to the reactor R1 by means of lines 7a, 3a and 9a, whereas line 7b remained closed.

The remaining 70.5 kg/hr of the mixture of $CO_2$/air, were sent from line 9, by means of lines 9c and 9d, to the exchanger SC1, which they leave by means of line 3 at a temperature of 197° C., by heat exchange with the $CO_2$ stream coming from line 2 at 200° C. and which exits at 185° C. by means of line 6. Said $CO_2$/air mixture was sent to the stripper S1 from line 3, through line 3b.

A liquid stream 11, consisting of the flowing products, was discharged from the bottom of the stripper S1:
Urea=1,000 kg/hr
$H_2O$=500 kg/hr
$CO_2$=170 kg/hr
$NH_3$=480 kg/hr
which was sent to the subsequent urea purification and concentration steps. These substantially consist of the typical medium- and low-pressure separation sections, and the concentration section, characterizing the traditional Urea SNAMPROGETTI Process, whose general scheme is shown, for example, on page 561 of the publication "Encyclopaedia of Chemical Technology" previously mentioned.

EXAMPLE 2

The process of example 1 was substantially repeated, with the difference that the $CO_2$ stream containing air, fed to the bottom of the stripper by means of line 15b, was characterized by the following composition:
$CO_2$=50 kg/hr
Air=0.36 kg/hr This stream was also heated to a temperature of 197° C. by passage through the intersteps of the compressor, according to the following scheme, different from that of example 1.

733 kg/hr of fresh $CO_2$ in a mixture with 5.5 kg/hr of air, were compressed to 16.2 MPa and heated to 110° C. by passage through the four compression steps C1, C2, C3 and C4. The whole of the $CO_2$ stream (738.5 kg/hr) and air leaving C4 by means of line 9, was sent to the exchanger SC3, by means of line 9b, which it leaves by means of line 7, at a temperature of 150° C. due to the effect of the thermal exchange with the $CO_2$ stream coming from line 5 at 190° C., which exits by means of line 6 at 125° C.

An aliquot of said stream leaving SC3 by means of line 7, consisting of 50.36 kg/hr, was sent, by means of line 7b, to the exchanger SC1 and from there, further heated to 197° C., by the effect of the thermal exchange with the $CO_2$ stream coming from line 2 at 200° C. and which it leaves by means of line 4 at 195° C., it was sent to the stripper S1 by means of lines 3 and 3b, corresponding to line 15b of FIG. 2. The remaining part of the stream of line 7, consisting of 688.14 kg/hr, was sent directly to the reactor R1, at a temperature of 150° C., by means of lines 7, 7a, 3a and 9, corresponding to line 15a of FIG. 2. The line 9c remained closed.

Due to the variation in the flow-rate of the stream fed to the bottom of the stripper by means of line 15b, from 70.50 kg/hr to 50.36 kg/hr, the quantities of $CO_2$ in lines 13, 14 and 17 of FIG. 2, correspondingly decrease by about 20 kg/hr with respect to example 1.

EXAMPLE 3

The process of example 1 was substantially repeated, with the difference that the $CO_2$ stream containing air, fed to the bottom of the stripper by means of line 15b, was characterized by the following composition:

$CO_2$=30 kg/hr
Air=0.21 kg/hr

This stream was also heated to a temperature of 183° C. according to the following scheme, different from that of example 1.

733 kg/hr of fresh $CO_2$ in a mixture with 5.5 kg/hr of air, were compressed to 16.2 MPa and heated to 110° C. by passage through the four compression steps C1, C2, C3 and C4. The whole of the $CO_2$ stream (738.5 kg/hr) and air leaving C4 by means of line 9, was sent to the exchanger SC3, by means of line 9b, which it leaves by means of line 7, at a temperature of 147° C. due to the effect of the thermal exchange with the $CO_2$ stream coming from line 5 at 190° C., which exits by means of line 6 at 127° C.

The whole stream leaving SC3 by means of line 7, was sent, by means of line 7b, to the exchanger SC1 and there further heated to 183° C., by the effect of the thermal exchange with the $CO_2$ stream coming from line 2 at 200° C. and which exits by means of line 4 at 150° C. A significant part of 30.21 kg/hr of the stream leaving SC1, by means of line 3, was sent to the stripper S1 by means of lines 3 and 3b, whereas the remaining part of 703.29 kg/hr, was sent to the reactor R1, still at a temperature of 183° C., by means of lines 3a and 9a. Lines 9c and 7a remained closed.

Due to the variation in the flow-rate of the stream fed to the bottom of the stripper by means of line 15b, from 70.50 kg/hr to 30.21 kg/hr, the quantities of $CO_2$ in lines 13, 14 and 17 of FIG. 2 correspondingly decrease by about 40 kg/hr with respect to example 1.

Tests of the process carried out according to the above examples for an operating period of 1 year, did not produce any significant corrosion phenomena, even without a separate feeding of the passivating agent to the stripper.

The invention claimed is:

1. An enhanced process for the synthesis of urea from ammonia and carbon dioxide, at a high pressure and temperature, with the formation of ammonium carbamate as an intermediate, which includes a high-pressure synthesis section, comprising at least one separation of the unconverted ammonium carbamate by decomposition-stripping with ammonia, carried out in vertical equipment, commonly called a stripper, wherein said separation also comprises a feeding of a $CO_2$ stream in the lower part of said stripper, said stream being, heated to a temperature ranging from 130 to 230° C. in a quantity of 1 to 15% by weight with respect to the total weight of the fresh $CO_2$ fed to the process, and containing a passivating agent in such a quantity that its equivalent content of $O_2$ in moles varies from 0.05% to 0.80% with respect to the moles of $CO_2$ of said stream.

2. The process according to claim 1, wherein the heated $CO_2$ stream fed to the stripper has a temperature ranging from 150 to 210° C.

3. The process according to claim 1, wherein the heated $CO_2$ stream fed to the stripper has a temperature ranging from 160 to 200° C.

4. The process according to claim 1, wherein the heated $CO_2$ stream fed to the stripper is in a quantity ranging from 3 to 12% by weight with respect to the total weight of the fresh $CO_2$ fed to the process.

5. The process according to claim 1, wherein the heated $CO_2$ stream fed to the stripper is in a quantity ranging from 4 to 12% by weight with respect to the total weight of the fresh $CO_2$ fed to the process.

6. The process according to claim 1, wherein the $CO_2$ stream fed to the reactor has a temperature ranging from 100 to 200° C.

7. The process according to claim 1, wherein both the $CO_2$ stream fed to the stripper and the $CO_2$ stream fed to the reactor are subjected to heating.

8. The process according to claim 1, wherein the fresh $CO_2$ is compressed in a multistep compressor equipped with thermal exchange intersteps.

9. The process according to claim 8, wherein the $CO_2$ stream fed to the bottom of the stripper is heated in one or more of the intersteps of said $CO_2$ compressor.

10. The process according to claim 8, wherein at least an aliquot of the $CO_2$ stream fed to the reactor is heated in one or more of the intersteps of the $CO_2$ compressor.

11. The process according to claim 8, wherein the $CO_2$ stream fed to the reactor consists of a mixture in suitable percentages of a compressed $CO_2$ stream and a $CO_2$ stream heated in at least the interstep of the compressor which has the highest thermal level.

12. The process according to claim 8, wherein the $CO_2$ stream fed to the reactor, having a temperature ranging from 130 to 185° C., consists, for a quantity ranging from 0 to 40% by weight with respect to the total weight of said stream, of compressed $CO_2$ leaving the reactor at a temperature ranging from 100 to 120° C., and for a quantity ranging from 60 to 100% by weight with respect to the total weight of said stream, of a $CO_2$ stream heated in one or more of the thermal exchange intersteps of the compressor, up to a temperature ranging from 140 to 200° C.

13. The process according to claim 8, wherein the $CO_2$ stream fed to the stripper, representing from 4 to 12% by weight of the $CO_2$ sent to the reactor, is heated to a temperature ranging from 160 to 200° C. in one or more of the thermal exchange intersteps of the $CO_2$ compressor.

14. The process according to claim 8, wherein the $CO_2$ stream subjected to heating is heated in one or more of the intersteps of the $CO_2$ compressor, at the outer side or tube side.

15. The process according to claim 1, wherein the decomposition-stripping of ammonium carbamate with ammonia is a self-stripping step.

16. The process according to claim 1, wherein the passivating agent is present in such an amount that its equivalent content of $O_2$ in moles ranges from 0.10 to 0.40% with respect to the $CO_2$ moles of said stream.

17. The process according to claim 1, wherein the passivating agent is an oxidant.

18. The process according to claim 17, wherein the oxidant is selected from air, oxygen, enriched air, hydrogen peroxide or mixtures thereof.

19. The process according to claim 17, wherein the oxidant is air.

20. The process according to claim 1, wherein it includes a synthesis phase of urea, wherein the ammonia/carbon dioxide molar ratio is between 2.7 and 5.0.

21. A plant for effecting the enhanced synthesis process of urea, according to claim 1, comprising a synthesis section wherein a reactor is connected with a stripper, suitable for operating under "self-stripping" conditions, connected, in turn, in its lower part, with the separation and purification section of urea, and in its upper part to the condenser of the carbamate, which, in turn, is connected with the reactor, wherein said reactor is also connected to a compressor for the feeding of fresh carbon dioxide, said compressor is also connected with the lower part of said stripper for transferring a $CO_2$ stream to the stripper in a quantity of 1 to 15% by weight with respect to the total fresh $CO_2$ fed to the plant.

22. The plant according to claim 21, wherein it is obtained by modifying a pre-existing plant for the synthesis of urea, equipped with a stripper suitable for operating under self-stripping conditions, by preparing a connection line between the $CO_2$ compressor and the lower part of said stripper, suitable for feeding a $CO_2$ stream to the stripper itself in a quantity ranging from 1 to 15% by weight with respect to the total weight of the fresh $CO_2$ fed to the plant.

* * * * *